United States Patent
Ramsteiner (10) Patent No.: US 10,036,702 B2
(45) Date of Patent: Jul. 31, 2018

(54) METHOD, DEVICE AND SENSOR FOR DETERMINING AN ABSORPTION BEHAVIOR OF A MEDIUM

(71) Applicant: Robert Bosch GmbH, Stuttgart (DE)

(72) Inventor: Ingo Ramsteiner, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/975,799

(22) Filed: Dec. 20, 2015

(65) Prior Publication Data

US 2016/0178508 A1 Jun. 23, 2016

(30) Foreign Application Priority Data

Dec. 22, 2014 (DE) .................. 10 2014 226 827

(51) Int. Cl.
*G01N 21/00* (2006.01)
*G01N 21/31* (2006.01)
*G01N 21/85* (2006.01)

(52) U.S. Cl.
CPC .......... *G01N 21/31* (2013.01); *G01N 21/314* (2013.01); *G01N 21/8507* (2013.01); *G01N 2201/0662* (2013.01); *G01N 2201/0668* (2013.01)

(58) Field of Classification Search
CPC .... A61B 5/0091; A61B 5/4312; G01N 21/31; G01N 21/314; G01N 2201/0668
USPC ........ 356/432, 319, 336, 437; 600/437, 328, 600/407
See application file for complete search history.

(56) References Cited

U.S. PATENT DOCUMENTS

| | | | | |
|---|---|---|---|---|
| 4,023,909 A | * | 5/1977 | Ross | G01N 21/85 250/575 |
| 5,293,873 A | * | 3/1994 | Fang | A61B 5/0091 600/437 |
| 5,828,687 A | * | 10/1998 | Colgan | H01S 3/034 372/92 |
| 7,826,050 B2 | * | 11/2010 | DiFoggio | G01N 21/0303 356/241.1 |
| 2012/0038925 A1 | * | 2/2012 | Gahr | G01N 21/15 356/440 |

(Continued)

FOREIGN PATENT DOCUMENTS

JP         2006194775 A  *  1/2005  ............. G01N 21/59

OTHER PUBLICATIONS

Itabashi Yukihisa, JP2006194775 A, Jan. 14, 2005, Translation.*
RCA Corporation, RCA Electro-Optics Handbook, Copyright 1974, Technical Series EOH-11.*

*Primary Examiner* — Isiaka Akanbi
(74) *Attorney, Agent, or Firm* — Maginot, Moore & Beck LLP (57) ABSTRACT

A method is used to determine an absorption behavior of a medium. The method includes establishing an absorption coefficient of the medium using a first intensity value and at least one second intensity value and a length different between a first measurement distance and a second measurement distance. The first intensity value represents a measured first light intensity after passing over a first measurement distance in the medium. The second intensity value represents a measured second light intensity after passing over a second measurement distance in the medium. The first intensity value and the second intensity value are measured using light with a common initial intensity.

3 Claims, 5 Drawing Sheets

(56) References Cited

U.S. PATENT DOCUMENTS

| | | | | |
|---|---|---|---|---|
| 2013/0006088 A1* | 1/2013 | Miyasato | ............ | A61B 5/0073 600/407 |
| 2013/0211218 A1* | 8/2013 | Suzuki | ................ | A61B 5/1455 600/328 |
| 2016/0345837 A1* | 12/2016 | Takama | ............... | A61B 6/0414 |

* cited by examiner

METHOD, DEVICE AND SENSOR FOR DETERMINING AN ABSORPTION BEHAVIOR OF A MEDIUM

This application claims priority under 35 U.S.C. § 119 to patent application number DE 10 2014 226 827.3, filed on Dec. 22, 2014 in Germany, the disclosure of which is incorporated herein by reference in its entirety.

BACKGROUND

The present disclosure relates to a method for determining an absorption behavior of a medium, to a corresponding device, to a sensor for determining an absorption behavior of a medium and to a corresponding computer program.

An absorption behavior of a medium is described by an absorption coefficient of the medium.

SUMMARY

Against this backdrop, the approach presented here is used to present a method for determining an absorption behavior of a medium, a corresponding device which uses this method, a sensor for determining an absorption behavior of a medium and, finally, a corresponding computer program in accordance with the following description. Advantageous embodiments emerge from the following description.

A calculation equation for the absorption coefficient of a medium can be extended by a length difference between two measurement distances in the medium. By rewriting the equation, various interference factors can be eliminated from the equation. In particular, the measurement distances in the medium are dispensed with, so long as the length difference therebetween is known. Thus, the same medium can be transilluminated twice over different measurement distances when determining an absorption behavior or the absorption coefficient of the medium. Hence, the absorption of the medium can therefore be measured at at least two different measurement distances.

A method for determining an absorption behavior of a medium is presented, wherein the method comprises the following step:

establishing an absorption coefficient of the medium using a first intensity value and at least one second intensity value and a length different between a first measurement distance and a second measurement distance, wherein the first intensity value represents a measured first light intensity after passing over a first measurement distance in the medium and the second intensity value represents a measured second light intensity after passing over a second measurement distance in the medium, wherein the first intensity value and the second intensity value are measured using light with a common initial intensity.

The method can comprise a first step of measuring the first intensity value, a subsequent step of modifying the measurement distance by the length difference and a following second step of measuring the second intensity value. As a result of an integrated measurement process, the medium can be analyzed quickly and directly.

The light source can be operated in a pulsed fashion. The measurement distance can be modified in a pulsed fashion. A reference value of the intensity can be measured by a pulsed light source. The reference value can be calculated from the intensity values. As a result of the pulsed measurement distance, the first intensity value and then the second intensity value can be measured in a periodically alternating manner. As result, an approximately constant measurement is possible.

The first intensity value and the second intensity value can be measured using light in a common wavelength range. In particular, the intensity values can be measured using light from the same light source. What this can ensure is that the light has the same initial intensity.

Furthermore, a sensor is presented for determining an absorption behavior of a medium, with the sensor comprising the following features:

a light source for providing light;

a detector for detecting a light intensity of light incident on the detector; and an apparatus for modifying a variable measurement distance between the light source and the detector, wherein the medium is arrangeable within the measurement distance.

The modification apparatus can be embodied to move the light source relative to the detector. The measurement distance can be embodied as a gap between the light source and the detector. The modification apparatus can also modify a gap width and hence the measurement distance. Likewise, the light source and the detector can have a constant distance from one another. Then, a boundary of the gap can be moved in order to vary the measurement distance in the medium. As a result, the medium in the gap can be kept in motion in order to prevent the deposition of suspended matter. Moreover, this accelerates the exchange of the volume situated in the gap. The latter is advantageous in the case of very narrow gaps in particular, which inhibit the exchange by diffusion or inward flow.

The light source and the detector can be arranged stationary relative to one another. The modification apparatus can be embodied to move a movable reflector, which is embodied to reflect the light from the light source to the detector. As a result, a particularly robust sensor can be provided.

The light source can have an optical lens for shaping the light in the direction of the detector. A collimated beam path (parallel rays) of the light when passing through the medium is advantageous because then intensity density and beam cross section remain constant when the distance is modified. The detector can have a lens for concentrating the light from the light source onto the detector. The light intensity can be adapted in the medium to the medium by way of optically effective elements in the beam path.

The detector can have at least two light-sensitive regions. The regions can be sensitive to different wavelength regions of the light. This allows the measurement of the light absorption by the medium at different wavelengths, for example in order to quantify various absorption bands or in order to obtain reference values for a baseline correction.

The approach presented here furthermore provides a device for determining an absorption behavior of a medium, which is embodied to carry out, actuate or implement the steps of one variant of a method presented here in appropriate apparatuses. The object underlying the disclosure can also be achieved in a quick and efficient manner by this embodiment variant of the disclosure in the form of a device.

In the present case, a device can be understood to mean an electrical instrument which processes sensor signals and outputs control signals and/or data signals dependent thereon. The device can have an interface which can be embodied in terms of hardware and/or software. In the case of an embodiment in terms of hardware, the interfaces can be e.g. part of a so-called system ASIC, which contains very different functions of the device. However, it is also possible for the interfaces to be dedicated integrated circuits or at least partly consist of discrete components. In the case of an embodiment in terms of software, the interfaces can be software modules which e.g. are present on a microcontroller in addition to other software modules.

A computer program product or computer program with program code, which may be stored on a machine-readable medium or storage medium such as a semiconductor storage, a hard disk drive storage or an optical storage and which is used to carry out, implement and/or actuate the steps of the method according to one of the embodiments described above is also advantageous, in particular if the program product or program is executed on a computer or a device.

BRIEF DESCRIPTION OF THE DRAWINGS

The approach presented here is explained in more detail in an exemplary manner below on the basis of the attached drawings. In detail.

DETAILED DESCRIPTION

In the subsequent description of expedient exemplary embodiments of the present disclosure, the same or similar reference signs are used for the elements which are depicted in the various figures and which have a similar effect, with a repeated description of these elements being dispensed with.

Figure 1:
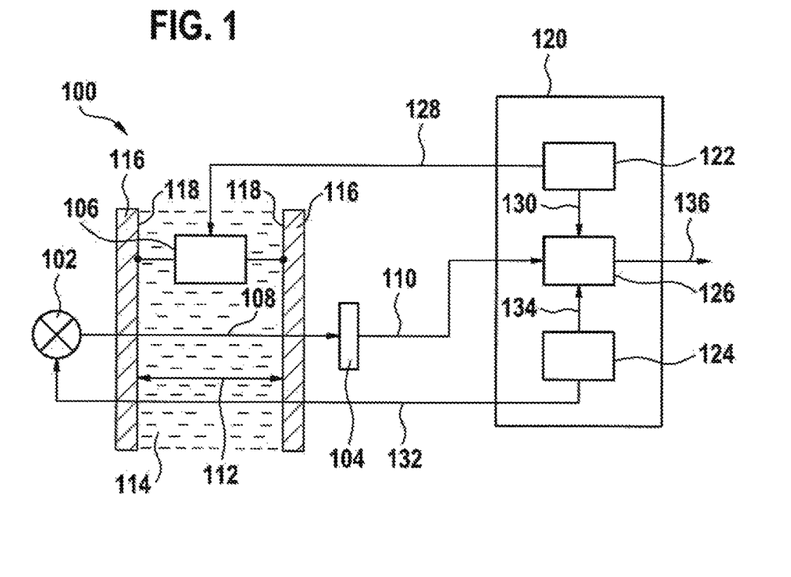
FIG. 1 shows a block diagram of a sensor for determining an absorption behavior in accordance with an exemplary embodiment of the present disclosure.

FIG. 1 shows a block diagram of a sensor 100 for determining an absorption behavior in accordance with one exemplary embodiment of the present disclosure. The sensor 100 has a light source 102, a detector 104 and a modification apparatus 106. The light source 102 is embodied to provide light 108. The detector 104 is embodied to detect a light intensity of light 108 incident on the detector 104 and to map this to an intensity value 110. The modification apparatus 106 is embodied to modify a measurement distance 112 between the light source 102 and the detector 104. A medium 114, the absorption behavior of which is intended to be determined, is arrangeable within the measurement distance 112.

In the depicted exemplary embodiment, the measurement distance 112 is defined by two panes 116 aligned substantially parallel to one another. The panes 116 are transparent to the light 108. In other words, the light source 102 is arranged behind a first pane 116 while the detector 104 is arranged behind a second pane 116. A gap 112 is situated between the panes 116. The modification apparatus 106 is coupled mechanically to the panes 116. The apparatus 106 can move either one of the panes 116 or both panes 116 in such a way that the gap 112 becomes narrower or broader. In the depicted exemplary embodiment, the modification apparatus 106 is decoupled from the light source 102 and the detector 104. Hence, a distance between the light source 102 and the detector 104 remains the same, even if the measurement distance 112 is modified.

When a medium 114 is arranged in the gap 112 and the light source 102 transmits the light 108 through the medium 114, the medium 114 absorbs at least a component of the light 108. Since an absorption between the light source 102 and the first pane 116, within the panes 116 and between the second pane 116 and the detector 104 is negligible, the intensity of the light 108 acquirable by the detector 104 merely depends on an initial intensity of the light 108 at the light source 102 and the absorption in the medium 114. The absorption in the medium 114 depends on the distance 112 between the surfaces 118 of the panes 116 and on an absorption coefficient of the medium 114.

In the approach presented here, the absolute distance 112 between the panes 116 or the path 112 which the light 108 has traveled in the medium 114 is not included in a calculation of the absorption coefficient. To this end, the sensor 100 is connected to a device 120 for determining an absorption behavior of a medium in accordance with one exemplary embodiment of the present disclosure.

The device 100 has a distance control apparatus 122 for the distance 112, a light-control apparatus 124 for the light source 102 and an establishment apparatus 126. The distance control apparatus 122 is connected to the modification apparatus 106 by way of a control line. The distance control apparatus 122 provides a distance signal 128 for the modification apparatus 106 by way of the control line. The distance signal 128 represents a modification request for the distance 112. A value 130 which represents the distance modification or a length difference 130 between two measurement distances 112 is provided for the establishment apparatus 126. The light-control apparatus 124 is connected to the light source 102 by way of a control line. The light-control apparatus 124 provides a light signal 132 for the light source 102 by way of the control line. The light signal 132 represents a status request of the light 108. The requested status 134 of the light 108 is provided for the establishment apparatus 126. In the establishment apparatus 126, the absorption coefficient 136 of the medium 114 is established using a processing prescription, the length difference 130, the status 134 of the light source 108 and at least two intensity values 110, which are acquired at different distances 112.

In other words, FIG. 1 shows an optical media sensor 100 with a variable measurement gap 112. Here, the principle of a sensor 100, which determines the optical absorption behavior of a medium 114 by means of a light-transmission measurement, is depicted schematically.

The medium 114 is a liquid or a gas, which fills the space 112 between the two windows 116 which, in turn, are transparent to the light 108 used for the measurement. The light 108 is produced by a light source 102, it enters the medium 114 through an entry window 116, passes therethrough, emerges through the exit window 116 and it is incident on a detector element 104. The light intensity I 110 detected there allows the absorption coefficient α of the medium 114 to be determined in accordance with the Beer-Lambert law.

$$I = I_0 e^{-\alpha d}$$

Here, d is the path length d 112 in the medium 114 and $I_0$ is the light intensity that would fall on the detector 104 without absorption in the medium 114.

Usually, the absorption $\alpha(\lambda)$ is of interest at a specific wavelength $\lambda$ or at a defined number of individual wavelength $\lambda_1$, $\lambda_2$, $\lambda_3$, .... Here, as is the case below, "wavelength $\lambda$" always means a wavelength interval with a finite width centered about $\lambda$.

In practice, not all transmission losses can be ascribed to the absorption coefficient $\alpha$ of the medium 114 alone. For example, coatings may form at the window surfaces 116 over time or the windows 116 themselves may tarnish due to material aging. Both can lead to additional absorption or scattering. All these effects lead to an additional attenuation factor $A(\lambda)$ that is independent of the optical path length d 112 and the more precisely worded Beer-Lambert law is as follows:

$$I(\lambda) = I_0(\lambda) A(\lambda) e^{-\alpha(\lambda) d}.$$

Figure 9:
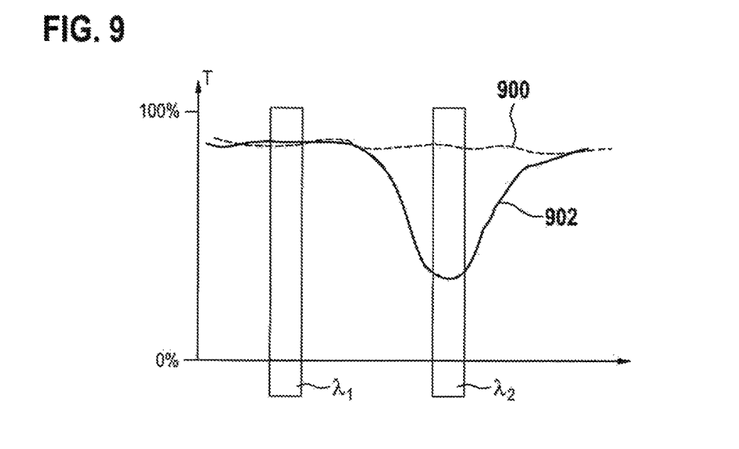
FIG. 9 shows transmission curves of different media.

In laboratory spectrometers, $I_0(\lambda)$ and $A(\lambda)$ are determined by means of a reference measurement on a non-absorbing (reference) medium. However, this is not usually possible for a sensor 100 in the field, which is installed in a line or a tank. However, if the variables are unknown, a simple measurement at $\lambda_2$ does not suffice for determining $\alpha(\lambda_2)$, as depicted in FIG. 9, and hence for determining the concentration of the analyte.

Only forming the ratio of the transmitted intensities 110 in both wavelengths $$I(\lambda_2)/I(\lambda_1) = I_0(\lambda_2)/I_0(\lambda_1) \cdot A(\lambda_2)/A(\lambda_1) \cdot e^{-(\alpha(\lambda_2) - \alpha(\lambda_1))d}$$

allows the correction of these effects under the conditions that the ratio $I_0(\lambda_2)/I_0(\lambda_1)$ is known and stable in time and that the ratio $A(\lambda_2)/A(\lambda_1)$ is known and stable in time.

By way of example, the ratio of the intensities 110 is not provided if two separate light-emitting diodes which exhibit different aging properties are used. By way of example, the ratio of the attenuation factors is not provided if a coating which exhibits a different absorption behavior at the two wavelengths forms on the windows 116.

Therefore, if these conditions are satisfied and the optical path d is known, it is possible to determine $(\alpha(\lambda_2) - \alpha(\lambda_1))$.

In our example, $(\alpha(\lambda_1) = 0)$, but the previous discussion can easily be generalized. In practice, there is a basic absorption at all wavelengths which is independent of the analyte 114. Either it is known or it can be derived from the measurement of further wavelengths. What applies in principle is that the more wavelengths are considered, the more unknowns can be eliminated in relation to the measurement device and the medium.

In practice, sensor concepts often fail due to the fact that the aforementioned conditions are precisely not satisfied. Causes for this already specified include different aging properties of the sources or spectrally inhomogeneously absorbing window coatings, but the list could be arbitrarily extended, for example temporal variations in the emission characteristic of an individual source 102 and therefore different light distributions on the detector elements 104, wavelength-dependent scattering effects as a result of material aging or particle depositions on the window 116.

In the approach presented here, all influences independent of d 112 on the measured intensity 110 are eliminated by varying the optical light path d 112. As a result, aging and dirtying effects of the hardware, a reduction in the wavelengths to be measured and/or an improvement in the reliability as a result of correspondence of the measurement variables and a compensation of manufacturing tolerances and/or a reduction in the calibration outlay can be achieved.

In particular, sensors are presented in which the light paths d 112 are very short due to strongly absorbent media 114, and so variations in the light path d 112 can be brought about by piezo-elements 106. Specific applications are infrared-optical measurements of liquids 114, very specifically the determination of the proportion of ethanol in gasoline or fatty acid methyl esters (FAME) in diesel fuels.

In general, a sensor 100 in accordance with the approach presented here comprises a device 106 which permits variation of the light path d 112 in the medium 114, i.e. the distance 112 between the media-facing window surfaces 118, by a difference $\delta$.

If two measurements are carried out over d and $(d+\delta)$ for the same wavelength $\lambda$, the following is obtained by forming a ratio:

$$\frac{I(\lambda, d)}{I(\lambda, d+\delta)} = \frac{I_0(\lambda) A(\lambda)}{I_0(\lambda) A(\lambda)} \frac{e^{-\alpha(\lambda) d}}{e^{-\alpha(\lambda)(d+\delta)}} = e^{-\alpha(\lambda) \delta}.$$

Provided that the adjustment path d is known, the absorption coefficient a is the only unknown in this equation. Even the absolute path d is no longer contained therein, and so e g manufacturing tolerances no longer have to be compensated for by calibration. Thus, in the ideal case, $\alpha(\lambda)$ can be determined by a measurement at a single wavelength.

In principle, the above-described principle can be applied wherever the absorption or attenuation coefficient of a gaseous or liquid medium 114 is intended to be measured.

In particular, non-dispersive infrared spectroscopy (NDIR) of liquids, in particular of fuels, is described.

Here, the absorption lengths 112 are extremely short (<1 mm). The required adjustment path d in the 10 μm range can thus be implemented in a precise, long-term reproducible and wear-and-tear-free manner by piezo-actuators 106.

In the approach presented here, possible coating formation on the windows 116 is not included in the calculation of the absorption coefficient. As a result of the independence of the calculation from the absolute measurement distance 112, the sensor 110 can be operated without calibration.

Likewise, the number of wavelength channels can be reduced by the approach presented here. Since the bandpass filters make up a significant portion of the costs in cost-effective embodiments of a sensor 100 with a thermal radiation source 102 and one detector 104 per wavelength, the price of the sensors scales directly with the number of wavelengths to be acquired.

In one exemplary embodiment, FIG. 1 describes a variant of a sensor 100 for determining the content of fatty acid methyl esters (FAME) in biodiesel blends.

The sensor 100 comprises a thermal radiation source 102, which is configured as a filament 102 or micro-hotplate 102. Furthermore, the sensor comprises a detector 104, which is embodied as a microbolometer 104, a thermopile 104 or in a pyroelectric manner. The detector 104 is embodied including a bandpass filter for a wavelength $\lambda = 5.7$ μm, with a FWHM of 100 to 500 nm, more particularly 200 nm.

Optionally, the sensor 100 has a second detector with a bandpass filter for a wavelength $\lambda = 4$ μm, 4.5 μm or 5.3 μm and a FWHM as above.

The absorption path d 112 is ten micrometers to 100 μm, in particular 30 μm. By means of a piezo-actuator 106, it is possible to set an adjustment path $\delta$ of one micrometer to 20 μm, in particular five micrometers.

In one exemplary embodiment, the sensor 100 has a second detector 104 with a bandpass filter for wavelength λ of four micrometers, 4.5 μm or 5.3 μm.

In one exemplary embodiment, the sensor 100 has a source 102 and a detector 104 as described above. However, in this case, the bandpass filter is configured for a wavelength λ of 4.9 μm, with a FWHM of 100 to 300 nm, more particularly 200 nm. The measurement distance d 112 lies between 100 and 1000 μm, more particularly at 200 μm. The distance difference δ lies between one micrometer and 50 μm, more particularly 20 μm.

In one exemplary embodiment, the sensor 100 has a second detector 104 with a bandpass filter for a wavelength λ of four micrometers or 4.5 μm.

Figure 2:
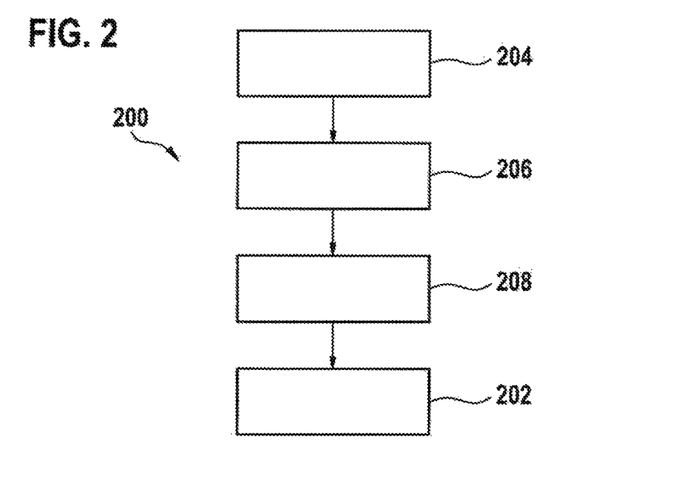
FIG. 2 shows a flowchart of a method for determining an absorption behavior in accordance with an exemplary embodiment of the present disclosure.

FIG. 2 shows a flowchart of a method 200 for determining an absorption behavior of a medium in accordance with an exemplary embodiment of the present disclosure. The method 200 can be carried out using a sensor, as is depicted in e.g. FIG. 1, and a device, as is depicted in e.g. FIG. 1. The method 200 has an establishment step 202. An absorption coefficient of the medium is established in the establishment step 202 using a first intensity value and at least one second intensity value and a length difference. The first intensity value represents a measured first light intensity after passing over a first measurement distance in the medium. The second intensity value represents a measured second light intensity after passing over a second measurement distance in the medium. The first measurement distance differs from the second measurement distance by the length difference. The first intensity value and the second intensity value are measured using light with a common initial intensity.

The method 200 can comprise a first step 204 of measuring the first intensity value, a subsequent step 206 of modifying the measurement distance by the length difference and a following second step 208 of measuring the second intensity value. The steps 204, 206, 208 are carried out prior to the establishment step 202.

Figure 3:
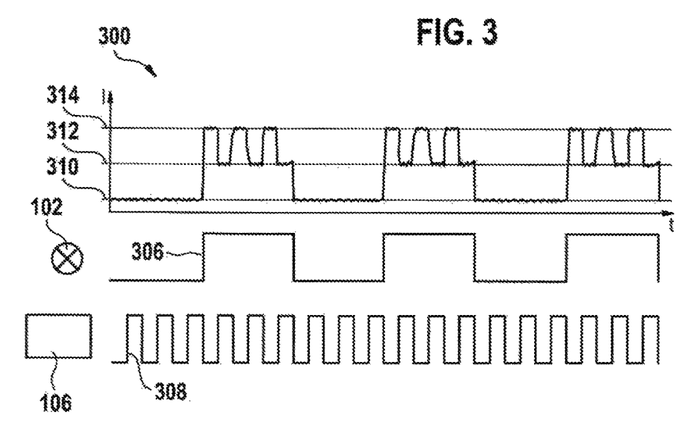
FIGS. 3 to 5 show operating schemes for operating a sensor in accordance with one exemplary embodiment of the present disclosure.
Figure 4:
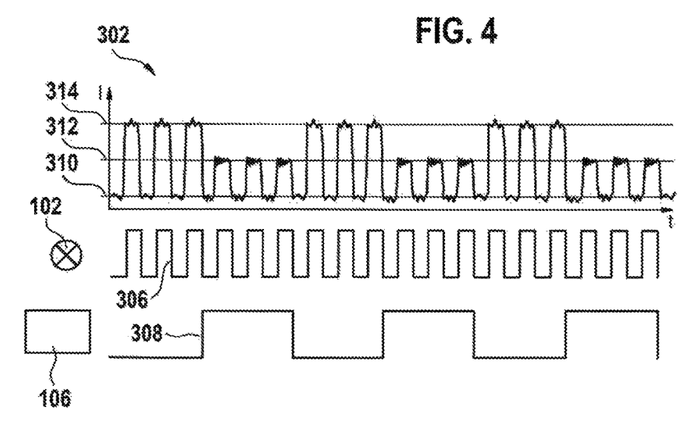
Figure 5:
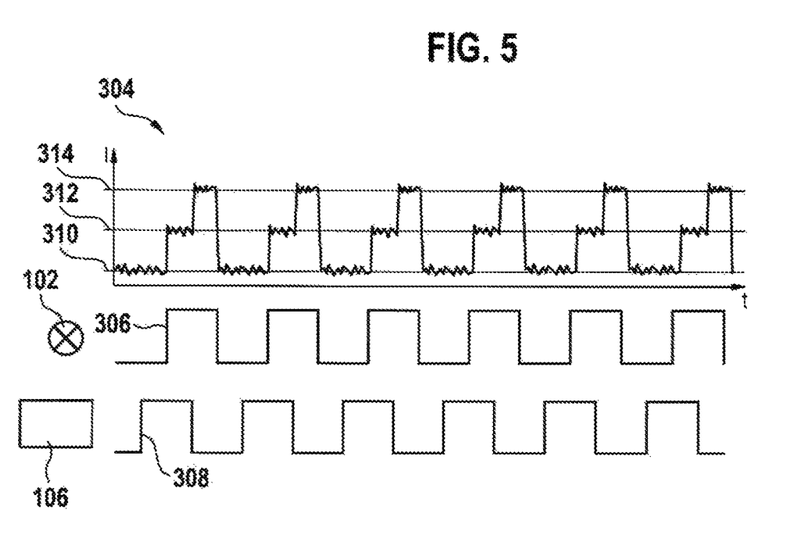

FIGS. 3 to 5 show operating schemes 300, 302, 304 for operating a sensor in accordance with one exemplary embodiment of the present disclosure. In accordance with the operating schemes 300, 302, 304 depicted here, a sensor, as is depicted e.g. in FIG. 1, can be actuated by means of a device, as is depicted in e.g. FIG. 1. Three mutually independent operating schemes 300, 302, 304 are depicted. What is shown for each operating scheme 300, 302, 304 is a light intensity I over time t and a light signal 306 or the control signal 306 for the light source 102 over time t and a distance signal 308 or the control signal 308 for the modification apparatus 106 over time t. The light source 102 and the modification apparatus 106 are operated in a pulsed manner in all operating schemes 300, 302, 304. As a result, the light intensity I can have three different values 310, 312, 314. A first light intensity 310 sets in when the light source 102 is inoperative. By way of example, the first light intensity 310 represents stray light, which is coupled into the sensor by the medium. Likewise, the first light intensity 310 represents dark noise of the detector. A second light intensity 312 and a third light intensity 314 set in when the light source 102 is in operation. Here, the two light intensities 312, 314 are different in terms of their value. The value is dependent on the path which the light travels in the medium. Hence, the light intensity I depends on the measurement distance in the medium set by the modification apparatus 106 when the light source 102 is in operation. However, a ratio between the second light intensity 312 and the third light intensity 314 is dependent in this case on the length difference between the transilluminated paths. This length difference is known.

The light source 102 is operated in a pulsed manner with a low frequency in the first operating scheme 300. The modification apparatus 106 is operated in a pulsed manner with a high frequency. Here, the frequency of the distance signal 308 is three times as high as the frequency of the light signal 306. As a result, the light intensity I changes six times while the light source 102 is switched on. In other words, the second intensity value 314 is acquired three times and the third intensity value 314 is acquired three times within one light pulse. Only the first intensity value 310 is acquired when the light source 102 is dark.

The light source 102 is operated in a pulsed manner with the high frequency in the second operating scheme 302. The modification apparatus 106 is operated in a pulsed manner with the low frequency. Here, the frequency of the light signal 306 is three times as high as the frequency of the distance signal 308. As a result, the light source 102 is respectively activated three times while the measurement distance is increased or decreased. Hence, the acquired light intensity I varies between the first intensity value 310 and the second intensity value 312 while the measurement distance is increased. The acquired light intensity I varies between the first intensity value 310 and the third intensity value 314 while the measurement distance is reduced.

The light source 102 and the modification apparatus 106 are operated with the same mean frequency in the third operating scheme 304. Here, the light pulses are offset from the movement pulses by a quarter period. Hence, the measurement distance in each case changes in the middle of a light pulse. What results from this is a step-like increase in the light intensity I from the first intensity value 310, when the light source 102 is off, via the second intensity value 312, when the light source 102 is on and the measurement distance is increased, to the third intensity value 314, when the measurement distance is reduced. Then, the light intensity I falls back to the first intensity value when the light source 102 is switched off.

What is advantageous in all embodiments is that the light source is operated in a pulsed manner, as is conventional in optical sensor systems. Measurements with a switched-off source are recommended in any case to correct for dark currents of the detectors and possible stray light influences from foreign sources in the surroundings. Moreover, by way of a correlation of the measured intensity with the actuation signal of the source, pulsed operation allows improvement in the signal-to-noise ratio and a lock-in amplification.

Since the absorption path d is also varied, at least three different intensities I occur at a detector element. Here, the three intensities represent light off, light on and distance d, light on and distance d+δ. Three exemplary operating schemes 300, 302, 304 are illustrated in FIGS. 3 to 5.

In the first operating scheme 300, the period of the mechanical distance change is shorter than that of the radiation pulses. This operation is advantageous if the source has slow dynamics, which is particularly true in the case of thermal sources.

In the second operating scheme 302, the radiation pulses have a higher frequency than the distance change. Depending on design, what is advantageous here is lower material fatigue because there are fewer mechanical cycles over the service life of the sensor.

In the third operating scheme, the mechanical and optical actuations have the same frequency but are phase-shifted. The sampling rate of all three intensities is relatively high in this case, which is good for quickly changing measurements but it makes the evaluation more complicated.

Moreover, the gas dynamics or hydrodynamics of the medium should be considered when selecting the mechanical frequency since mechanical length changes simultaneously play a role for the interchange of the sample volume and have an effect on the dynamics of the sensor, particularly in the case of narrow measurement gaps.

Figure 6:
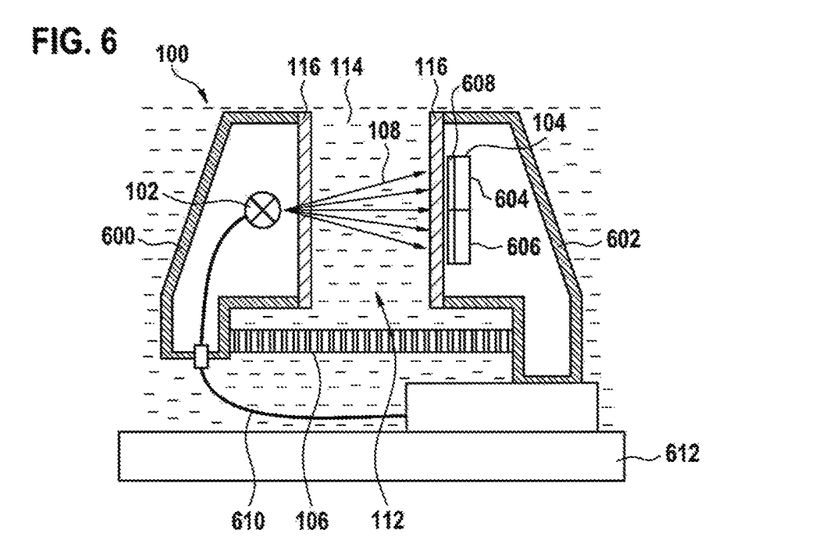
FIG. 6 shows an illustration of a sensor for determining an absorption behavior in accordance with one exemplary embodiment of the present disclosure.

FIG. 6 shows an illustration of a sensor 100 for determining an absorption behavior of a medium 114 in accordance with one exemplary embodiment of the present disclosure. The sensor 100 substantially corresponds to the sensor of FIG. 1. In contrast thereto, the light source 102 and the detector 104 are respectively arranged in separate housing parts 600, 602. The housing parts 600, 602 are movable relative to one another as a whole in order to change the measurement distance 112. The modification apparatus 106 in this case is a piezo-actuator 106. The piezo-actuator 106 connects the housing parts 600, 602 to one another. When an electric voltage is applied to the piezo-actuator 106, a length of the piezo-actuator 106 changes proportional to a value of the applied voltage.

In the depicted exemplary embodiment, the first housing part 600 has a movable embodiment. The second housing part 602 has a stationary embodiment.

The housing parts 600, 602 are media-tight or fluid-tight. The side faces of the housing parts 600, 602 facing the gap 112 or the measurement distance 112 are sealed by panes 116.

The light source 102 is an incandescent light source 102 and provides light 108 with a broad frequency spectrum. The detector 104 is embodied to detect light 108 in a first spectral range and in a second spectral range. The spectral ranges differ from one another. To this end, the detector 104 has a first portion 604 and at least one second portion 606. The portions 604, 606 are arranged next to one another behind the second pane 116. A first filter 608 which filters out, or at least substantially attenuates, wavelengths or frequencies of the light 108 outside of the first spectral range is arranged between the second pane 116 and the first portion 604. A second filter 608 which filters out, or at least substantially attenuates, wavelengths or frequencies of the light 108 outside of the second spectral range is arranged between the second pane 116 and the second portion 604. Thus, the first portion 604 is embodied with the first filter 608 to detect light 108 in the first spectral range. The second portion 606 is embodied with the second filter 608 to detect light 108 in the second spectral range.

The light source 102 is connected by way of a flexible cable 610. The cable bridges the gap 112 freely in the medium 114 and it is guided into the housing 600 by way of a media-tight passage.

A wavelength selectivity can also be established by virtue of one or more inherently narrow-band light sources, i.e., for example, light-emitting diodes or laser diodes, being used.

In the depicted exemplary embodiment, use is made of bandpass filters 608, as can be realized, for example, by dielectric layer systems on the basis of interference effects. These filters 608 can be placed into the beam path 108, either on the side of the light source(s) 102 or on the side of the detector 104 or a detector array 104.

A thermal emitter, for example with a filament 102, can be used as a broadband light source 102. Then, e.g. two detectors 104, which are covered by different bandpass filters 608 such that one of them is sensitive to light with the wavelength $\lambda_1$, while the other one is sensitive to $\lambda_2$, can be used and hence it is possible to carry out two transmission measurements.

$$I(\lambda_i) = I_0(\lambda_i) e^{-\alpha(\lambda_i) d}.$$

A non-dispersive infrared (NDIR) sensor 100 measures the optical transmissivity of a liquid or gaseous medium 114. "Non-dispersive" means that, in view of an implementation that is as simple as possible and cost-effective, it is not continuous spectra that are measured with a high resolution, but precisely only selected wavelengths $\lambda$ in the near ($\lambda$=600-2500 nm) or mid-($\lambda$=2500-20 000 nm) infrared range (NIR and MIR).

Technically, an NDIR sensor 100 consists of one or more radiation sources 102, such as e.g. a thermal emitter, light-emitting diodes or laser diodes, one or more detectors 104 sensitive to the relevant radiation 108, such as e.g. thermopiles, pyroelectric elements or bolometers, also photodiodes in the NDIR range, and an absorption path 112 lying between source 102 and detector 104, which is at least partly pervaded by the medium 114.

With a few exceptions, such as LEDs or laser diodes, neither source 102 nor detector 104 are spectrally selective. In order to restrict the spectral range, use is then mainly made on the detector side of interferometric bandpass filters 608.

The approach described here extends the above-described principle by a variable absorption path 112. Specifically, embodiments are described with a thermal radiation emitter 102 as a source 102 and two detector elements 104 not specified in any more detail, which are provided with two different bandpass filters 608. This is a liquid sensor 100. The absorption of the medium 114 is at least so high at one of the relevant wavelengths that the absorption path d 112, i.e. the width of the gap 112 filled by the medium 114, may be significantly shorter than 1 mm. The variation $\delta$ lies in the 10 µm range and it is technically implemented by a piezo-element 106.

However, this specific embodiment is merely a special application-relevant example. The approach presented here can be applied to any other combination of any number of sources 102 and detector elements 104, irrespective of the specific technology on which these components are based and irrespective of whether they are provided with bandpass filters 608.

FIG. 6 schematically shows an embodiment of a sensor 100 with two detector units 604, 606, respectively covered by two different bandpass filters 608. These components are housed in a housing part 602, which is connected to the inner wall 612 of a tank or a line in a rigid and stationary manner. The radiation source 102 is situated in a separate housing part 600, which is movable at a distance in relation to the first one 602. Both housing parts 600, 602 have radiation-transmissive windows 116, which are parallel to one another at a distance d 112 and the interspace therebetween 112 is pervaded by the medium 114 to be characterized, which surrounds the sensor 100. The mechanical connection between the two housing parts 600, 602 is configured in such a way that the distance d 112 between the windows 116 can be varied by a value $\delta$, while the parallel property thereof is maintained; in the specific example, this can be brought about by changing the length of a piezo-actuator 106 which connects the housing parts 600, 602. Additional means such as guide rails, clamps, bellows, springs or other flexible connections are not depicted here, but can be used to stabilize the parallel property of the windows 116 and relieve the piezo-actuator 106 from shearing, bending and torsional forces. The power supply of the source 102 can be implemented by means of a flexible line 610, which optionally can additionally fulfill a mechanical stabilization function.

Figure 7:
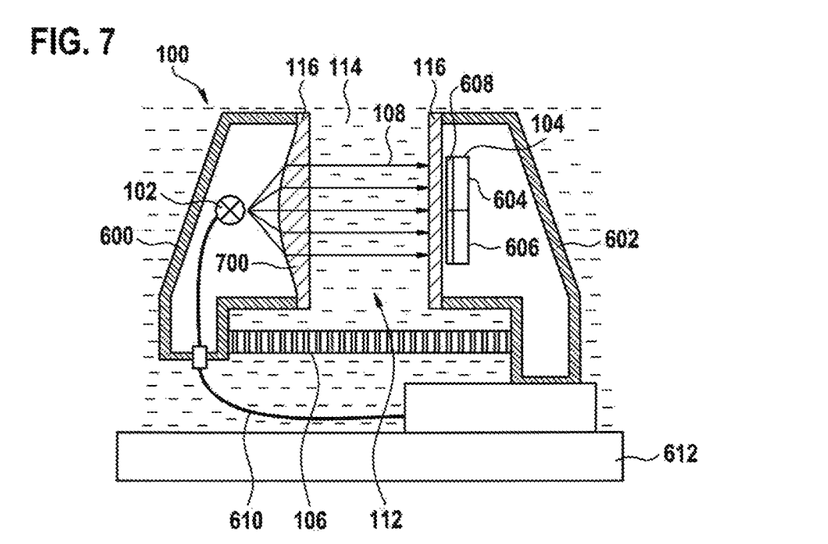
FIG. 7 shows an illustration of a sensor for determining an absorption behavior in accordance with a further exemplary embodiment of the present disclosure.

FIG. 7 shows an illustration of a sensor 100 for determining an absorption behavior of a medium 114 in accordance with a further exemplary embodiment of the present disclosure. The sensor 100 substantially corresponds to the sensor from FIG. 6. Additionally, the first pane 116 between the light source 102 and the gap 112 is embodied as an optical element 700. In the depicted exemplary embodiment, the pane has a thickening in the region of the light source 102, which acts as a converging lens 700. The optical lens 700 aligns the divergent light 108, provided by the light source 102, approximately in parallel, or collimates the latter, in the region of the gap 112. As a result, the measurement distance 112 in the gap 112 is approximately equal for all light rays 108.

What was ignored in the derivation of the equations presented here is that the change in the distance between source 102 and detector 104, which is essential in this case, can already lead to a change in the detected intensity for ray-optical reasons because, of course, the solid angle covered by the detector 104 changes from the view of the source 102. Whether this effect occurs and how strong it is depends on the specific embodiment. It would be particularly pronounced in the case of a punctiform, isotropically radiating source 102, where it would lead to a quadratic intensity dependence. However, the effect is easily calculable at small distance variations δ and it can be compensated for in the data evaluation. If the source 102 is large compared to the overall distance, it may even be possible to completely ignore this effect for small δ.

By integrating a lens 700 as an additional element between source 102 and window 116, it is possible to collimate the radiation 108 directed to the detectors 104, or form said radiation into parallel beams, such that small distance variations δ do not play any role. FIG. 7 depicts an embodiment in which the window 116 itself is embodied as a lens 700. It is not mandatory, but advantageous, for the arching to be provided on the inner side of the component 600 in this case, while the side of the lens window 116 facing the medium 114 is planar. In this manner, the beam path 108 remains independent of the possibly variable refractive index of the medium 114.

In an exemplary embodiment not depicted here, lens elements are also integrated on the detector side in order to concentrate radiation 108 onto the detector surface.

Figure 8:
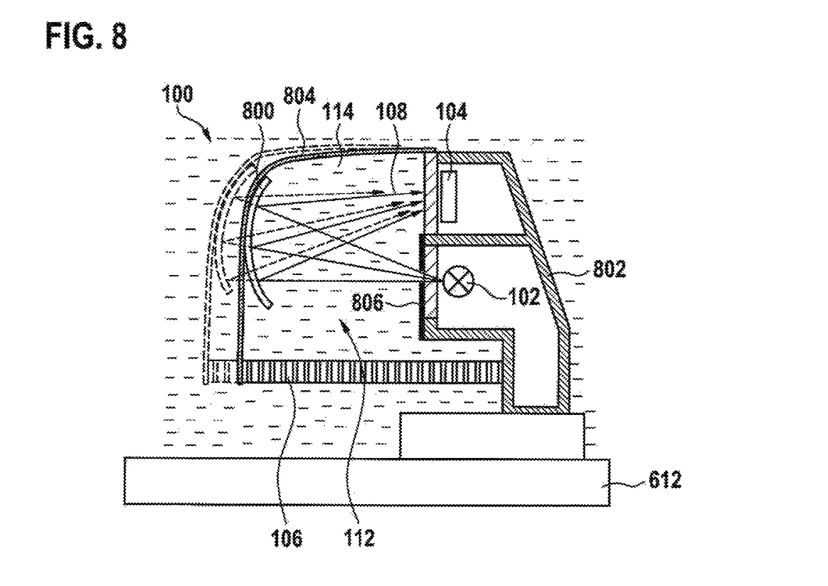
FIG. 8 shows an illustration of a sensor with a movable reflector in accordance with one exemplary embodiment of the present disclosure.

FIG. 8 shows an illustration of a sensor 100 with a movable reflector 800 in accordance with one exemplary embodiment of the present disclosure. The sensor 100 corresponds substantially to the sensor in FIG. 1. In contrast thereto, the light source 102 and the detector 104 are arranged on the same side of the gap 112 in a common housing 802 in this case. The reflector 800 is arranged on the other side of the gap 112. The modification apparatus 106 is coupled to the reflector 800 and the housing 802 and it is embodied to move the reflector 800 relative to the housing 802. The light 108 is therefore cast through the medium 114 from the light source 102 onto the reflector 800. There, the light 108 is reflected and cast onto the detector 104. In the process, the light 102 once again passes through the medium 114. A movement of the reflector 800 therefore has twice the effect on the path 112 passed over by the light 108 in the medium 114.

As an alternative to the previously shown embodiments, it is also possible—as shown in FIG. 8—to house the source 102 and detector(s) 104 in a common housing part 802. The radiation 108 from the source 102 is then guided onto the detector or detectors 104 by way of a mirror 800, which is preferably embodied as a hollow mirror 800. The space between the mirror 800 and the housing part 802 is pervaded by the medium 114 to be characterized. In this case, the mirror 800 has a movable arrangement, for example by way of an elastic spring 804, and it can be deflected by a mechanical actuator 106, for example a piezo-actuator 106, as a result of which the path 112 of the radiation 108 through the medium 114 changes by a small difference δ.

What is critical in relation to the other embodiments in this case is a more complex beam path, which harbors the risk of the amount of light falling on the detector 104 already changing for reasons of geometric optics, i.e. independently of the absorption in the medium 114. This can be counteracted by virtue of the light cone 108 being restricted so far by way of a stop 806 that all emitted light rays 108 are incident on the mirror 800, independently of the position thereof. In other words, the cross section of the beam 108 is completely covered by the mirror surface 800. Furthermore, the curvature of the mirror 800 is configured in such a way that it guides the radiation 108 onto the detector 104 in its entirety in all envisage d positions of the mirror 800.

FIG. 9 shows transmission curves 900, 902 of various media. The transmission curves 900, 902 are plotted in a diagram which plots the wavelength spectrum on the abscissa. The ordinate plots a transmission T in percent. The two transmission curves 900, 902 represent a light transmissivity of two different media over the wavelength spectrum. Two wavelength ranges $\lambda_1$, $\lambda_2$ are plotted in the diagram. The wavelength ranges $\lambda_1$, $\lambda_2$ are plotted at a distance from one another.

The first medium has no substantial absorption over the whole wavelength spectrum, which is why the first transmission curve 900 of the first medium is substantially constant at 90 percent.

The second medium has substantial absorption in the region of the second wavelength range $\lambda_2$. The second transmission curve 902 therefore substantially corresponds to the first transmission curve 900. In contrast thereto, the second transmission curve 902 has a minimum in the second wavelength range $\lambda_2$. Here, the second transmission curve 902 falls to approximately 40 percent.

By considering both wavelength ranges $\lambda_1$, $\lambda_2$, it is possible to distinguish between the two transmission curves 900, 902 and therefore between the different media in a sensor in accordance with one exemplary embodiment of the present disclosure.

In the example illustrated in FIG. 9, 900 is the transmission curve $T=I\lambda/I_0(\lambda)$ of a medium which has no absorption ($\alpha(\lambda)=0$) in the whole measurement range. 902 is the curve of the same medium, but now with the addition of a substance (the "analyte"), which absorbs light at $\lambda_2$, but not at $\lambda_1$.

The exemplary embodiments, which were described and shown in the figures, are only selected in an exemplary manner Different exemplary embodiments can be combined with one another in their entirety or in relation to individual features. It is also possible for an exemplary embodiment to be complemented by features of a further exemplary embodiment.

Furthermore, the method steps presented here can be carried out repeatedly and in a sequence that differs from the one described here.

If an exemplary embodiment comprises an "and/or" link between a first feature and a second feature, this should be read as meaning that the exemplary embodiment has both the first feature and the second feature in accordance with one embodiment and either only the first feature or only the second feature in accordance with a further embodiment.

What is claimed is:

1. A sensor for determining an absorption behavior of a medium, the sensor comprising:
   a housing comprising a first pane and a reflector, the housing being configured to hold a medium between the first pane and the reflector;
   a light source configured to emit light through the first pane and the medium without interruption to the reflector;
   a detector configured to detect a light intensity of light incident on the detector that is reflected from the reflector and through the medium without interruption to the first pane and to the detector; and
   a modification apparatus operatively connected to at least one of the first pane and the reflector, the modification apparatus being configured to move at least one of the first pane and the reflector between a first predetermined distance and a second predetermined distance; and
   a control device configured to:
      measure a first light intensity through the medium using the detector, the first light intensity corresponding to detected light emitted from the light source through the first pane and through the medium in a configuration where the first pane and the reflector are located at the first predetermined distance;
      measure a second light intensity through the medium using the detector, the second light intensity corresponding to detected light emitted from the light source through the first pane and through the medium in a configuration where the first pane and the reflector are located at the second predetermined distance; and
      identify an absorption coefficient of the medium based on the first intensity, the second intensity, and a difference between first predetermined distance and the second predetermined distance.

2. The sensor according to claim 1, wherein the light source has an optical lens configured to shape the light in a direction of the detector and/or the detector has a lens configured to concentrate the light from the light source onto the detector.

3. The sensor according to claim 1, wherein the detector has at least two light-sensitive regions, wherein the regions are sensitive to different wavelength regions of the light.

* * * * *